US006443897B1

(12) United States Patent
Dubberstein et al.

(10) Patent No.: US 6,443,897 B1
(45) Date of Patent: Sep. 3, 2002

(54) REFRACTION DELAY ERROR CORRECTION USING AGILE BEAMFORMER

(75) Inventors: David T. Dubberstein, Hales Corners; Steven C. Miller, Pewaukee, both of WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 54 days.

(21) Appl. No.: 09/750,869

(22) Filed: Dec. 28, 2000

(51) Int. Cl.[7] ................................................ A61B 08/00
(52) U.S. Cl. .......................... 600/447; 600/443; 73/625
(58) Field of Search ................................ 600/443, 447, 600/444, 448, 437; 72/602, 625, 626; 367/1, 10

(56) References Cited

U.S. PATENT DOCUMENTS 6,123,671 A 9/2000 Miller ........................ 600/447
6,210,332 B1 * 4/2001 Chiao et al. ................ 600/443
6,221,018 B1 * 5/2001 Ramamurthy et al. ...... 600/443
6,282,963 B1 * 9/2001 Haider ........................ 73/602

* cited by examiner

*Primary Examiner*—Marvin M. Lateef
*Assistant Examiner*—Maulin Patel
(74) *Attorney, Agent, or Firm*—Peter J. Vogel; Dennis M. Flaherty

(57) ABSTRACT

A method and an apparatus for correcting refraction delay errors on curved probes for all ranges using cordic rotation. The angle $\phi$ from the normal of an element to the focus is determined as a function of the angle of cordic rotation. Then a delay error correction is indexed using this angle $\phi$. The angular correction method is efficient in that it uses the inherent property of cordic rotation to calculate the only range-dependent variable required for the correction. Thus the additional hardware required to calculate the corrections is minimal, as the remaining correction variables are vector and range independent.

31 Claims, 8 Drawing Sheets

REFRACTION DELAY ERROR CORRECTION USING AGILE BEAMFORMER

FIELD OF THE INVENTION

This invention generally relates to coherent imaging methods which apply a phased array antenna. In particular, the invention relates to beamforming techniques for use in ultrasound imaging systems.

BACKGROUND OF THE INVENTION

A medical ultrasound system forms an image by acquiring individual ultrasound lines (or beams). The lines are adjacent to each other and cover the target area to be imaged. Each line is formed by transmitting an ultrasonic pulse in a particular spatial direction and receiving the reflected echoes from that direction. The spatial characteristics of the transmitted wave and the characteristics of the receive sensitivity determine the quality of the ultrasound image. It is desirable that the ultrasound line gathers target information only from the intended direction and ignores targets at other directions. Conventional ultrasound imaging systems comprise an array of ultrasonic transducer elements which are used to transmit an ultrasound beam and then receive the reflected beam from the object being studied. Such scanning comprises a series of measurements in which the focused ultrasonic wave is transmitted, the system switches to receive mode after a short time interval, and the reflected ultrasonic wave is received, beamformed and processed for display. Typically, transmission and reception are focused in the same direction during each measurement to acquire data from a series of points along an acoustic beam or scan line. The receiver is dynamically focused at a succession of ranges along the scan line as the reflected ultrasonic waves are received.

For ultrasound imaging, the array typically has a multiplicity of transducer elements arranged in one or more rows and driven with separate voltages. By selecting the time delay (or phase) and amplitude of the applied voltages, the individual transducer elements in a given row can be controlled to produce ultrasonic waves which combine to form a net ultrasonic wave that travels along a preferred vector direction and is focused in a selected zone along the beam. The beamforming parameters of each of the firings may be varied to provide a change in maximum focus or otherwise change the content of the received data for each firing, e.g., by transmitting successive beams along the same scan line with the focal zone of each beam being shifted relative to the focal zone of the previous beam. In the case of a phased array, by changing the time delays and amplitudes of the applied voltages, the beam with its focal zone can be moved in a plane to scan the object. In the case of a linear array, a focused beam directed normal to the array is scanned across the object by translating the aperture across the array from one firing to the next.

The same principles apply when the transducer probe. is employed to receive the reflected sound in a receive mode. The voltages produced at the receiving transducer elements are summed so that the net signal is indicative of the ultrasound reflected from a single focal zone in the object. As with the transmission mode, this focused reception of the ultrasonic energy is achieved by imparting separate time delay (and/or phase shifts) and gains to the signal from each receiving transducer element. The time delays are adjusted with increasing depth of the returned signal to provide dynamic focusing on receive.

In a typical ultrasound system the beamformer control is a significant contributor to the performance and cost of the system. Dynamic receive delay and apodization control must be generated for each beam and channel at a high rate. Often as many as 512 beam channels are required for a high-end system with an update rate as high as 10 MHz. Calculating delays and apodization for an ultrasound beamformer during dynamic reception requires complex calculations including transcendental functions. Normally image quality is traded off for cost by using second or third-order approximations for these functions. Additionally, large memories are frequently used to store pre-calculated controls for predetermined beam positions and parameters. Using stored pre-calculated values limits the ability of the system to optimally readjust beam position or parameters dependent on scanning situations. Thus image quality is compromised to achieve faster control response times.

There are a wide variety of beamformer control designs currently in use. All use some combination of large parameter random access memories (RAMs), state machines, complex calculations and approximations. Thus they fall short in one or more areas: agility, cost or precision.

Agility means the ability to change the beamforming setup for an entire imaging configuration in a time much less than 1 sec. where the setup includes vector phase center (aperture) positions, steering angles, f-numbers, and focal positions, and the imaging configuration includes all vectors (beams) displayed on the imaging console. Agility also means the ability to begin receive delay computation in mid-flight, i.e., immediately before a deep region of interest.

A new beamforming architecture which does not require large memories for storing pre-calculated beamforming values, which works equally well with transducer arrays of any geometry, and which is agile, precise and low in cost was disclosed in U.S. Pat. No. 6,123,671. That patent discloses an architecture for calculating beamformer time delays and apodization values in real-time by using a cordic rotator (hereinafter "cordic"), a 'simple multiplier-less device used for polar-Cartesian conversions. The use of the cordic to directly calculate the root-sum-of-squares without approximation or complex logic;provides ideal performance and flexibility at low cost. The system may quickly re-optimize the beam positions and parameters without the need to recalculate large pre-stored memories or use rough approximations. More specifically, the cordic rotators are utilized calculate ultrasonic beamforming apodization weightings and time delays. Apodization weightings and time delays are calculated in a real-time, distributed and pipelined manner without the need for large memories or complex state machines. There are no inherent approximations. Precision may be easily controlled to be within the accuracy of the delay apparatus. When a transducer array is attached to the ultrasonic imaging system, the element positions are written into relatively small distributed memories. The element positions do not need to be reloaded except when the array geometry is changed. While imaging, a small number of parameters are broadcast before each transmission and during each reception. These parameters may include: focal position(s), multiplexer state(s), aperture position(s), aperture size(s) and vector angle(s). Simple logic, including cordics, combines these parameters to produce beamforming time delays and apodization. Focal position and apertures may be changed very quickly for an entire image, in milliseconds. The receive focal positions do not need to start at the skin-line or follow a straight line, as required by state machine approaches. Reception focus can begin in mid-flight, and be warped to compensate for parallel beamforming methods. In addition, the array geometry may take any form; it is not restricted to the conventional linear, convex and phase arrays.

Many modern ultrasound scanners use curved probes to increase field of view and sensitivity. One of the problems with curved probes is the delay error caused by the refraction of the ultrasonic waves within the lens of the probe. A known beamformer calculates the focusing delays by assuming the ultrasonic waves travel a straight line from the center of an element to the focus at an average speed assumed to be 1.54 mm/μsec. In reality the probe lens affects both the direction and speed at which the ultrasonic waves travel. Thus the aforementioned known beamformer has a refraction delay error which is particularly severe for curved probes. Any delay error will degrade the focusing of the ultrasound scanner.

Another known beamforming system attempts to correct for the refraction delay eror by using an adjusted "false" radius of curvature (ROC) for curved probes. This false ROC is only a partial solution as it only corrects the refraction delay errors at one range. There is a need for a method to correct for the refraction delay errors for all ranges.

SUMMARY OF THE INVENTION

The present invention is directed to a method and an apparatus for correcting refraction delay errors on curved probes for all ranges. In accordance with the preferred embodiment, an agile beamformer is utilized. However, the angular correction method of the invention could be implemented in other forms. The idea is based in part on the observation that, if the angle $\phi$ from the normal of an element to the focus can be determined, then a delay error correction can be indexed using this angle. In the prior art (false ROC) beamformer previously mentioned, it would be computationally expensive to calculate the angle $\phi$ as a function of range. But in the agile beamformer, determining the angle $\phi$ is a relatively straightforward process.

In accordance with the preferred embodiments of the invention, the agile beamformer corrects for the delay errors caused by refraction for all ranges by using an angular correction method. The angular correction method is efficient in that it uses the inherent property of the cordic rotators to calculate the only range-dependent variable required for the correction. This means the additional hardware required to calculate the corrections is minimal, as the remaining correction variables are vector and range independent. Furthermore, each delay calculator within the agile beamformer handles 16 channels, further decreasing the hardware impact of an angular correction scheme. The angular correction method in accordance with the preferred embodiment uses a lookup table (LUT) of 256 possible delay adjustments and reduces the delay error to less than 10 nsec for two known probe models.

DETAILED DESCRIPTION OF THE PREFERRED EMBODIMENTS

The present invention can be incorporated in any ultrasound imaging system employing beamforming. One example of the foregoing is a B-mode ultrasound imaging system, which. will be generally described before disclosing in detail the preferred embodiment of the invention.

Figure 1:
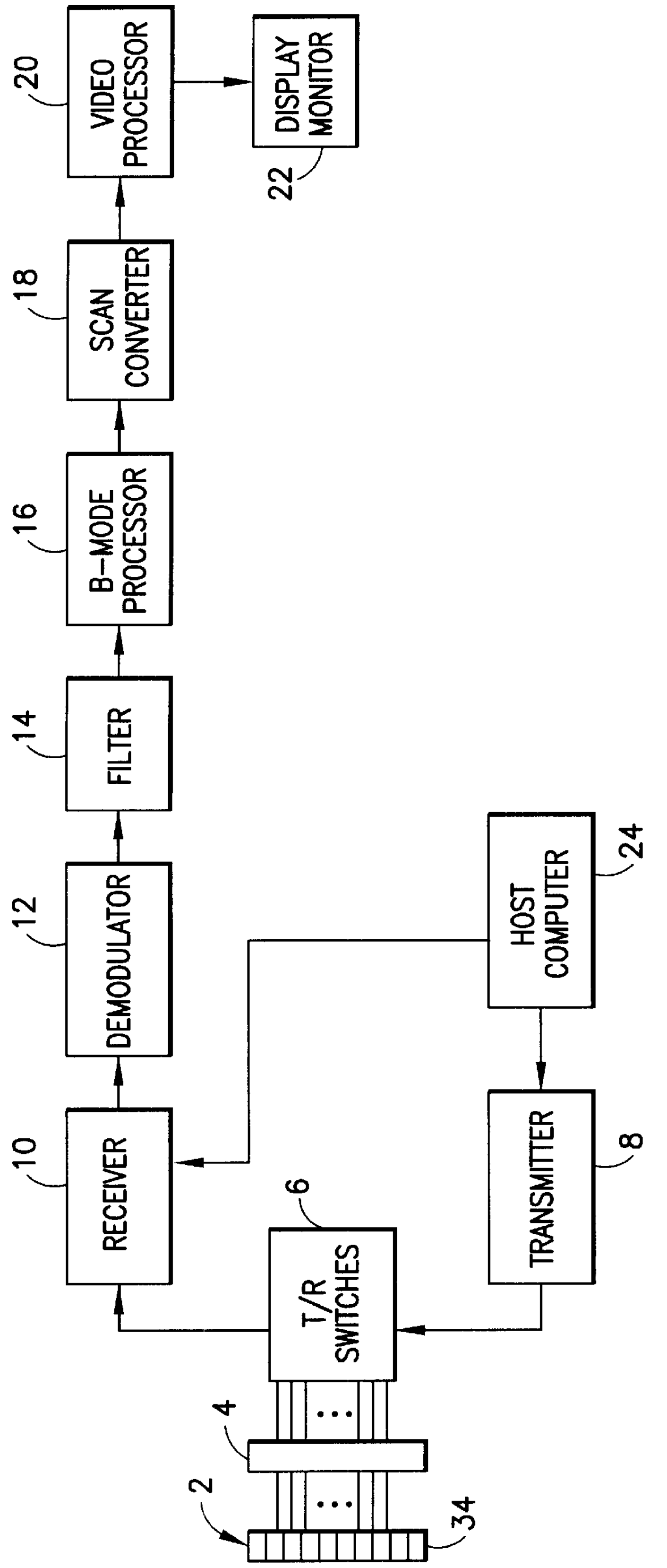
FIG. 1 is a block diagram showing a conventional ultrasound imaging system having a beamformer.

A conventional B-mode ultrasound imaging system is generally depicted in FIG. 1. The system comprises a transducer array 2 consisting of a plurality of separately driven transducer elements 34, each of which produces a burst of ultrasonic energy when energized by a pulsed waveform produced by a transmitter 8 and sent through a set of transmit/receive (T/R) switches 6 switched to a transmit state and respective switches of a multiplexer 4 switched to a MUX state. The ultrasonic energy reflected back to transducer array 2 from the object under study is converted to an electrical signal by each receiving transducer element 34 and applied separately to a receive beamformer 10 through the multiplexer switches 4 switched to the MUX state and the T/R switches 6 switched to a receive state. Transmitter 8 and receive beamformer 10 are operated under control of a host computer or master controller 24. A complete scan is performed by acquiring a series of echoes in which transmitter 8 is gated ON momentarily to energize each transducer element 34 in the transmit aperture, and the subsequent echo signals produced by each transducer element 34 are applied to receive beamformer 10. The receive beamformer 10 combines the separate echo signals from each transducer element 34 to produce a single echo signal which is used to produce a line in an image on a display monitor 22.

The receive beamformer's signal inputs are the low-level analog RF signals from the transducer elements 34. The receive beamformer is responsible for analog-to-digital conversion and for receive beamforming. In baseband imaging systems, the beamsummed signal is output to a demodulator 12, which converts the beamsummed signal into baseband in-phase I and quadrature Q receive beams. The I and Q acoustic data vectors from the demodulator 12 are sent to respective FIR filters 14 which are programmed with filter coefficients to pass a band of frequencies preferably centered at the fundamental frequency $f_0$ of the transmit waveform or a (sub)harmonic frequency thereof.

In the case of a B-mode imaging system, vectors of filtered I and Q acoustic data are sent to a B-mode processor 16, which converts the I and Q acoustic data into a log-compressed version of the signal envelope. The B-mode function images the time-varying amplitude of the envelope of the signal as a gray scale. The envelope of a baseband signal is the magnitude of the vector which I and Q represent. The I,Q phase angle is not used in the B-mode display.

The magnitude (i.e., intensity) of the signal is the square root of the sum of the squares of the orthogonal components, i.e., $(I^2+Q^2)^{1/2}$.

The B-mode amplitude data is output to a scan converter 18 comprising an acoustic line memory followed by an X-Y display memory. The acoustic line memory accepts the processed vectors of amplitude data and interpolates where necessary, and also performs the coordinate transformation of the amplitude data from polar coordinate (R−θ) sector format or Cartesian coordinate linear format to appropriately scaled Cartesian coordinate display pixel intensity data, which is stored in the X-Y display memory.

The scan-converted frames are passed to a video processor 20, which converts the pixel intensity data to the video frame rate and then maps the pixel intensity data to a gray-scale mapping for video display. A conventional ultrasound imaging system typically employs a variety of gray maps, which are simple transfer functions of the raw intensity data to display gray-scale levels. The gray-scale image frames are then sent to the display monitor 22 for display.

The ultrasound image produced by the system shown in FIG. 1 is composed of multiple image scan lines. A single scan line (or small localized group of scan lines) is acquired by transmitting focused ultrasound energy at a point in the region of interest, and then receiving the reflected energy over time. The focused transmit energy is referred to as a transmit beam. During the time after transmit, one or more receive beamformers coherently sum the energy received by each channel, with dynamically changing phase rotation or delays, to produce peak sensitivity along the desired scan lines at ranges proportional to the elapsed time. The resulting focused sensitivity pattern is referred to as a receive beam. A scan line's resolution is a result of the directivity of the associated transmit and receive beam pair.

The purpose of the beamformer is to provide maximum transmitted intensity and receive sensitivity at the desired. focal point(s) in space with minimum intensity/sensitivity away from the focal point(s). To do this, a beamformer must precisely calculate time delays which correspond to the difference in the propagation time of sound between the focal point(s) and elements of a transducer array. Typically the receive beamforming time delays are adjusted dynamically during reception. This allows the focal points to track the depth of the objects producing the received echoes. This depth is proportional to the time after transmission.

Figure 2:
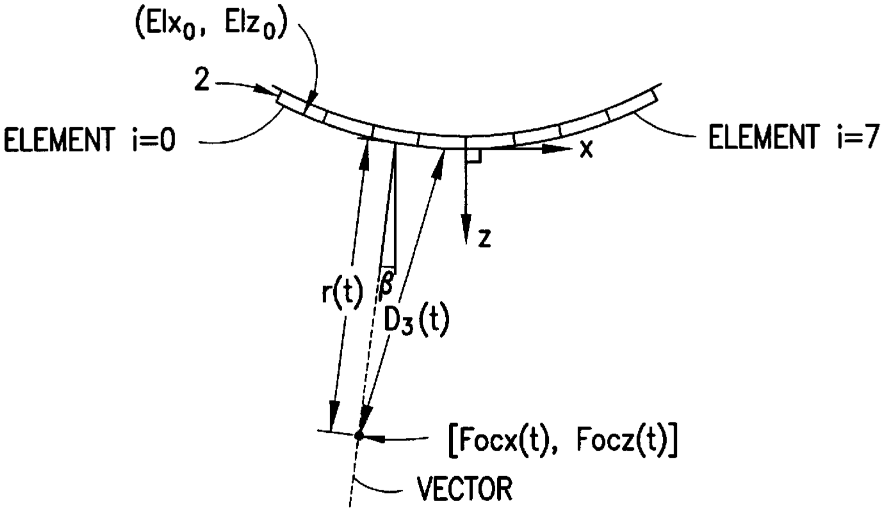
FIG. 2 is schematic showing the geometry of an ultrasound transducer array.

A typical transducer array geometry is shown in FIG. 2. In this example the elements of the array and the focal points all lie within a single plane in three-dimensional space. Thus one can describe the geometry in two dimensions: x and z, where the x axis is tangential to the center of the array face and the z axis is orthogonal to the x axis. The elements in the array are indexed by the letter "i". The position of each i-th element is indicated by its coordinates in x (azimuthal) and z (axial): $Elx_i$ and $Elz_i$, respectively. The vector along which the focal points lie may be described by an angle β, relative to the z axis. The position of the focal point, as a function of time, is indicated by coordinates Focx(t) and Focz(t). According to the Pythagorean Theorem, the propagation path length $D_i(t)$ is then:

$$D_i(t)=\mathrm{hypot}[(Elx_i-Focx(t)),\ (Elz_i-Focz(t))] \tag{1}$$

where hypot(x,z) is a function that calculates the hypotenuse of the two orthogonal lengths as defined below:

$$\mathrm{hypot}(x, z) \equiv \sqrt{x^2+z^2} \tag{2}$$

Some transducer arrays, referred to as two-dimensional arrays, have elements out of the x-z plane, in the elevational or y direction. For these arrays the geometry must. be extended with a y axis orthogonal to the x-z plane, with the positive direction pointing out of the plane of FIG. 1. The element position needs the additional coordinate of $Ely_i$. In addition, some modern systems acquire data in a three-dimensional volume where focal points may also be out of the x-z plane. Thus the additional coordinate of Focy(t) is required. In this more generalized case, the propagation path length $D_i(t)$ is $$D_i(t)=\mathrm{hypot}\{\mathrm{hypot}[(Elx_i-Focx(t)),\ Elz_i-Focz(t))],\ (Ely_i-Focy(t))\} \tag{3}$$

When an ultrasound imaging system is scanning, the receive focal point progresses from a point on the array face, along a line through the volume being imaged. This line is called a vector or beam. The point on the array face, at the intersection of the vector and the array, is called the vector phase center. The distance from the phase center to the focal point is r(t).

The beamformer delays the signals at each transducer element by a time $T_i(t)$ to compensate for the differences in propagation times. The propagation time is simply the propagation path distance divided by the speed of sound c (approximately 1.54 mm/μsec in tissue). Because the focal point is a function of time in reception, the delays are also a function of time. However, the delay at the phase center is kept constant to ensure a linear relationship between the depth of an object along the vector and the output of the corresponding echo signal from the beamformer. In addition, an offset delay is added to ensure the applied beamforming time delays are positive, a requirement to be causal. The beamforming delays are thus:

$$T_i(t) = T_{offset} + \frac{r(t)}{c} - \frac{D_i(t)}{c} \tag{4}$$

or $$T_i(t) = R_{offset}(t) - \frac{D_i(t)}{c} \tag{5}$$

where $$R_{offset}(t) = T_{offset} + \frac{r(t)}{c} \tag{6}$$

In addition to delays, the beamformer must provide apodization weightings or values which control the size and shading of the array active aperture. Apodization is applied according to the projection of the array onto a plane orthogonal to the vector. The apodization value for a particular element is determined by the projected distance from the center of the aperture divided by the projected aperture size. The aperture size and center may be controlled according to desired effective f-numbers and acceptance angles.

Figure 3:
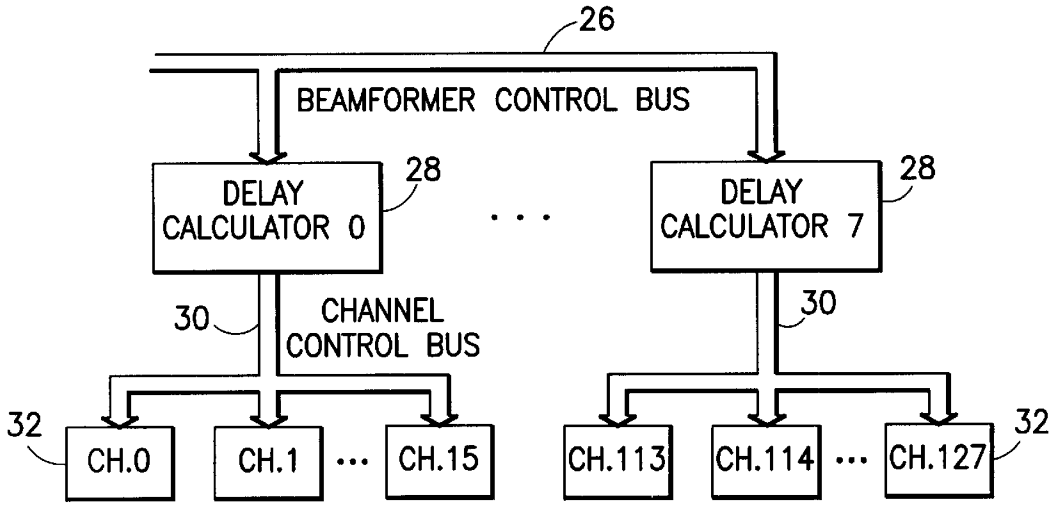
FIG. 3 is a block diagram showing an agile delay and apodization control architecture as disclosed in U.S. Pat. No. 6,123,671.

One embodiment, shown in FIG. 3, includes a plurality of delay calculators 28 distributed throughout the beamformer. Each delay calculator provides beamforming delays and apodization for a plurality of channels (32)/elements (34) via a channel control bus 30. The delay calculators are initialized with element position coordinates. Then, while imaging, focal coordinates and steering angles are broadcast to all delay calculators. All parameters may be provided to the delay calculators over a single beamformer control bus 26. The delay calculator uses a cordic to perform the aperture projections and carry out the hypot function. The cordic provides a very efficient and accurate means of performing the projection and calculating the hypotenuse. It performs successive coordinate transformations, in two dimensions, using coefficients that are simple powers of two. Thus it requires a small number of bit shifts and adds. It is pipelined, allowing high throughput. The resulting apodization values and time delays are then provided by a channel control bus 30 to a plurality of channels 32.

Figure 4:
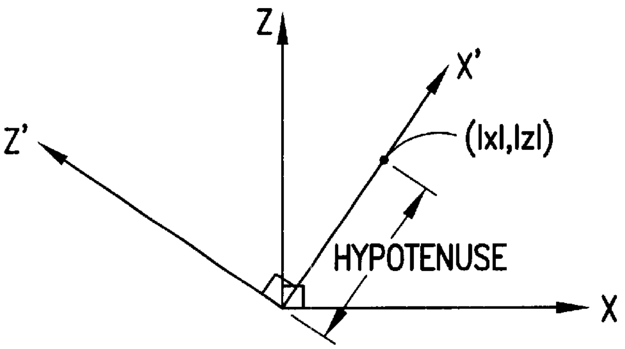
FIG. 4 is a schematic showing coordinate rotation for hypotenuse calculation.

Referring to FIG. 4, a hypotenuse can be calculated by first taking the absolute value of the coordinates, to put it in the first quadrant, then using the cordic to rotate it onto the x' axis (aligned with the hypotenuse to be calculated) and output the resulting x' value.

An apodization projection can be performed by simply rotating the coordinate system (see FIG. 5) about the origin by an angle −β, so that the z' axis is parallel with the vector. The transformed element x coordinates, $Elx'_i$, then provide the element position in the projection plane.

Figure 5:
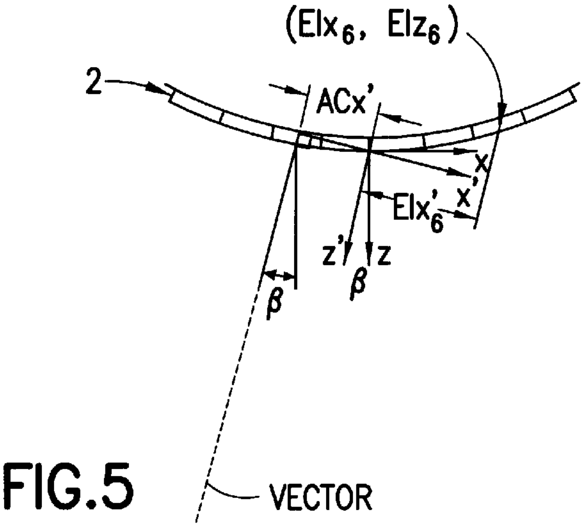
FIG. 5 is a schematic showing coordinate rotation for apodization projection.

The necessary calculation for apodization is the distance of an element from the aperture center, Acx', in the projection. Referring to FIG. 5, this distance is:

$$Apx_i = Acx' + Elx_i \tag{7}$$

The aperture center Acx' and the inverse aperture iAp are other parameters broadcast to all delay calculators. The product of $Apx_i'$ and the inverse aperture iAp is used to index a window function comprising a table of shading (apodization) values.

A hypotenuse in three dimensions may be calculated by two successive cordics. The first transforms x and z to a rotated coordinate system, x' and z'. The second then rotates x' and y to x" and y". The first cordic calculates the hypotenuse in the x-z plane by rotating it onto x', and the second cordic calculates the three-dimensional hypotenuse, now in the x'-y plane, by rotating it onto x". Similarly the apodization projection may be provided by first rotating the x and z axes about the y axes, and then rotating the y and x' axes about the z axis.

Figure 6:
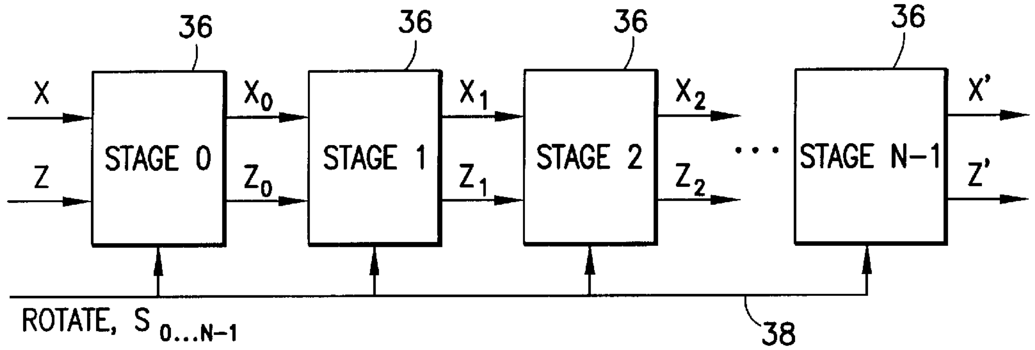
FIG. 6 is a block diagram showing an N-stage cordic rotator.
Figure 7:
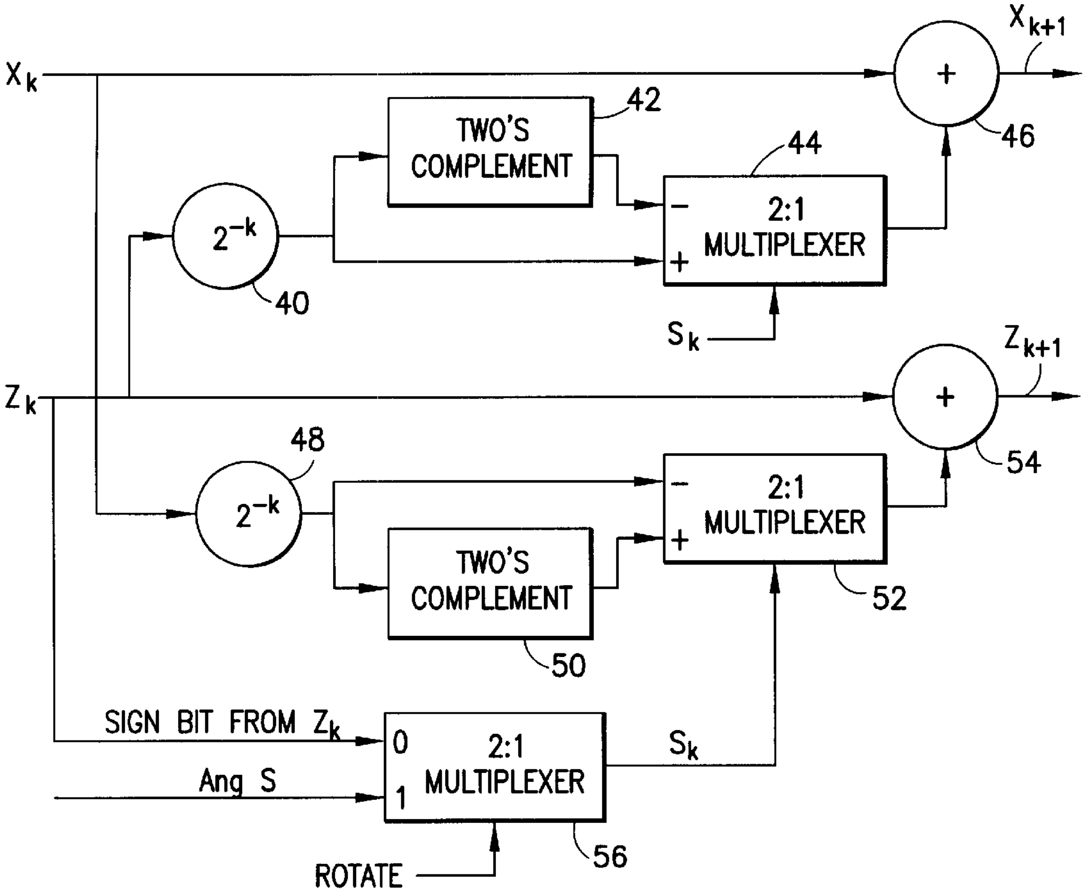
FIG. 7 is a block diagram showing a stage of a cordic rotator.

A cordic is composed of N stages as seen in FIG. 6. Given a stage index k=0 to (N−1), the coordinate transformation performed by each stage 36 of a cordic is:

$$\begin{bmatrix} x_{k+1} \\ z_{k+1} \end{bmatrix} = \begin{bmatrix} 1 & s_k 2^{-k} \\ -s_k 2^{-k} & 1 \end{bmatrix} \begin{bmatrix} x_k \\ z_k \end{bmatrix} \tag{8}$$

where $s_k = \pm 1$. This matrix multiplication is easily implemented with two adder/subtracters, as shown in FIG. 7. It produces a coordinate rotation of $$\theta_k = -s_k \arctan(2^{-k}) \tag{9}$$

and a magnification by $$M_k = \text{hypot}(1, 2^{-k}) \tag{10}$$

The total rotation after N stages is $$\theta = \sum_{k=0}^{N-1} \theta_k \tag{11}$$

and the total magnification is $$M = \prod_{k=0}^{N-1} M_k \tag{12}$$

The cordic shown in FIG. 7 can perform two functions: rotation of any input coordinates to the x' axis and rotation by a desired angle. The "rotate" control signal in FIG. 7 selects which of the two functions is performed.

When "rotate" is set to 1, the cordic rotates the inputs by an angle corresponding to the N sign bits, $s_0$ through $s_{N-1}$, provided at the input. This is used to project element positions onto a rotated axis for apodization. The rotate sign bits may be calculated according to the vector angle β prior to transmit and broadcast, as AngS, to all delay calculators 28 via the beamformer control bus 32 (see FIG. 3).

When "rotate" is zero, the cordic rotates the coordinates to the x' axis to provide the hypotenuse as x'. This is done by setting the sign bit $s_k$ at each stage to the sign bit of the input $z_k$. Thus the direction of rotation is always toward the x' axis. With each successive stage the angle of rotation becomes smaller and the hypotenuse asymptotically approaches the x' axis. The final x' output will be equal to the hypotenuse magnified by M, with the maximum remaining error determined by the smallest angle:

$$E_{max} = h_{max}(1 - \cos(\theta_{N-1})) \equiv h_{max} \times 2^{-2N+1} \tag{13}$$

where $E_{max}$ is the maximum remaining error and $h_{max}$ is the maximum hypotenuse. Given a maximum hypotenuse of 200 μsec and a maximum delay error of 6.25 nsec, an N=8 stage cordic is sufficient. The magnification factor is constant, independent of the angle of rotation; pre-scaling the inputs by 1/M provides an output with the correct scale.

The agile beamformer described above is agile, simple, and accurate. There are no vector- and element-dependent parameters. Vector-dependent parameters are element independent; element-dependent parameters are vector independent. The resulting small number of parameters allows for quick reprogramming. In addition, because there is no state machine, delay computation may begin anywhere along the vector. The cordic is inherently pipelined and extremely simple. It requires only a small number of adds/subtracts. Its precision is determined by the number of stages with no underlying approximation.

In accordance with the preferred embodiment shown in FIG. 3, the delay calculators 28 receive all the required parameters over a beamformer control bus 26. This control bus requires at least 16 data bits, 13 address bits and a "Start" bit. The "Start" signal resets the calculators for the beginning of a new vector. Transducer array geometry parameters are written before scanning, while vector parameters are written synchronous with scanning. For dynamic reception, this bus should run at 15 MHz. (For dual parallel beam reception, a 30-MHz bus or separate 15-MHz busses are required.) Separate, but nearly identical, control structures and busses may be used for transmit and receive.

There are three element position parameters required per element/channel combination, when a transducer is activated: ($Elx_i$, $Elz_i$, $Ely_i$). There are eight vector parameters which are updated during scanning: the focus position (Focx, Focz, Focy), the range offset ($R_{offset}$) the aperture center (ACx'), the inverse aperture size (iAp), the multiplexer state (MUX State), and the vector angle sign bits (AngS). For dynamic receive beamforming, the first six are updated during reception. If they are updated at a 2.5 MHz rate, then the resulting 2.5-MHz beamforming delay output can be linearly interpolated with adequate precision. This dictates the 15-MHz bus speed.

The MUX State is required when a multiplexer is used to connect different physical element(s) to individual channels. This is typical for large linear or convex transducers where the number of elements exceeds the number of beamforming channels. The element position corresponding to each delay channel then depends on the MUX State.

Each delay calculator 28 outputs delay and apodization information to a respective plurality of beamformer channels 32 through a respective channel control bus 30. For a 16-channel, single-beam delay calculator, this bus should have 16 data bits, 5 address bits and a "Strt" signal. The delay calculator outputs delay and apodization data interleaved by channel. Providing a 2.5 MHz update per channel, for 16 channels, requires a 40-MHz bus. Four address bits index the channels and one address bit indicates delay or apodization.

Figure 8A:
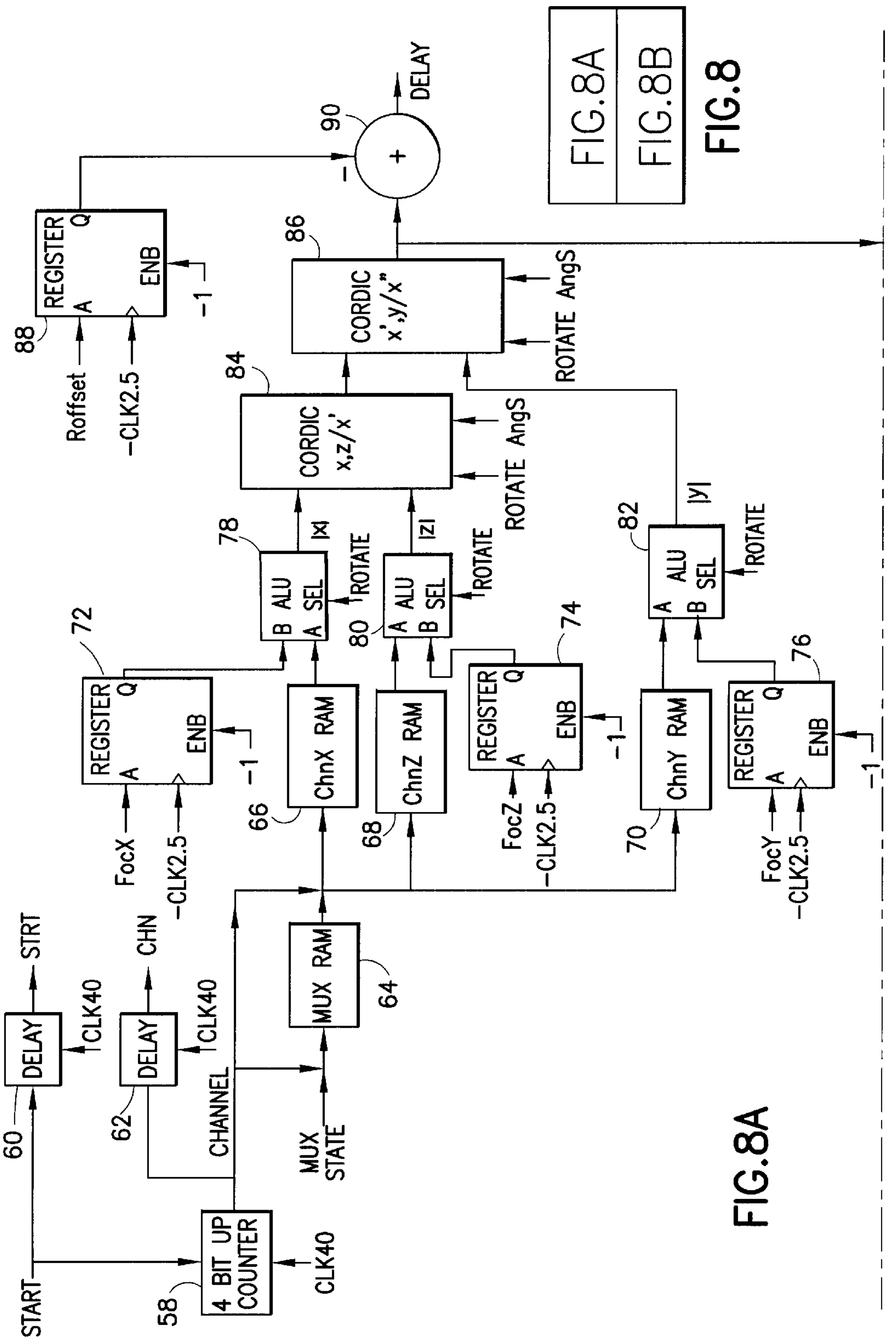
FIG. 8 is a block diagram in two parts (FIGS. 8A and 8B) showing a delay calculator in accordance with the preferred embodiment disclosed in U.S. Pat. No. 6,123,671.
Figure 8B:
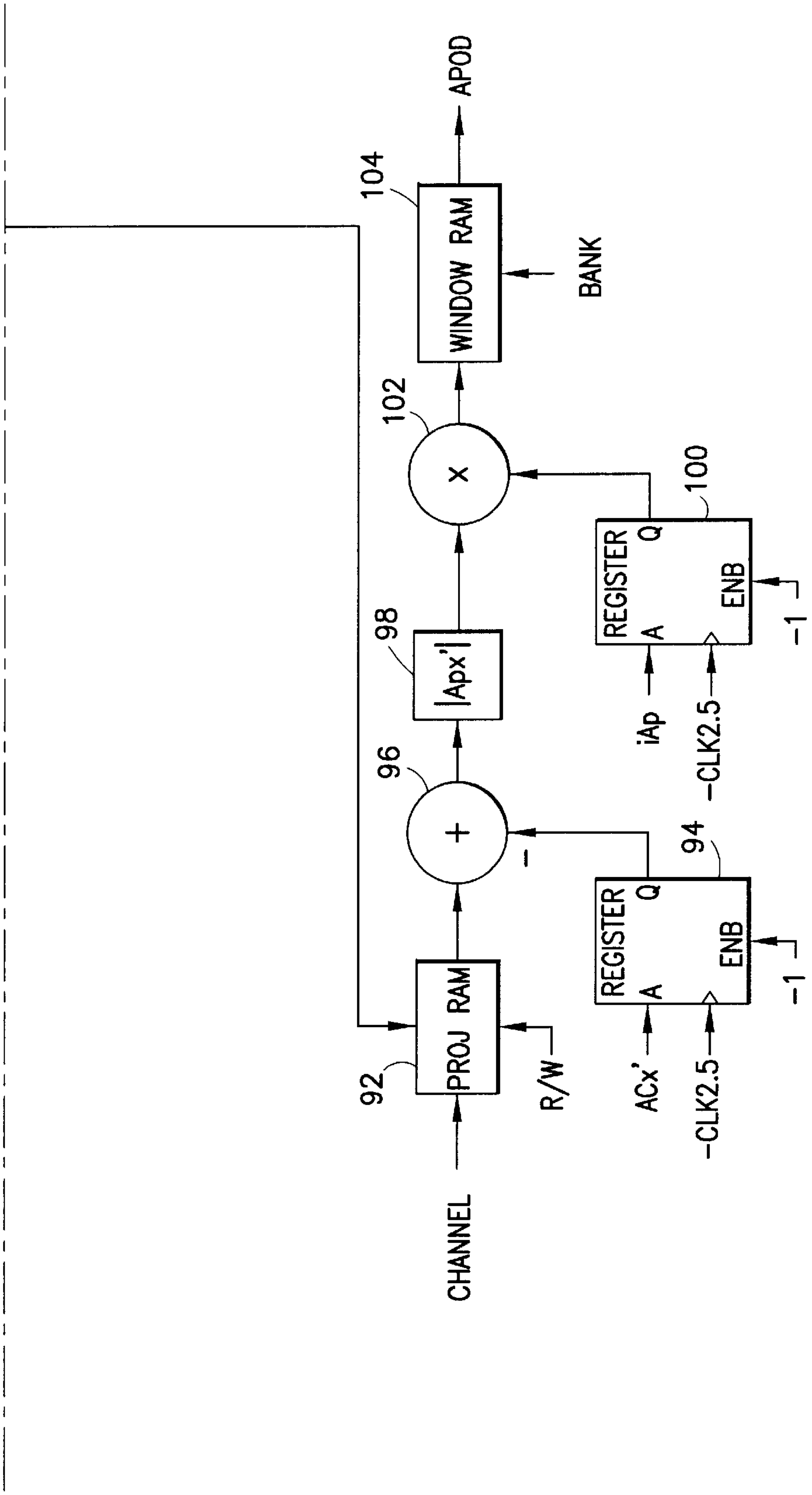

A delay calculator which does not incorporate the invention is shown in composite FIG. 8 (consisting of FIGS. 8A and 8B). This delay calculator provides delay and apodization for 16 channels. Four relatively small random access memories (RAMs) are used to store information about the activated array. This delay calculator provides 256 possible MUX states with a maximum of four physical elements associated with each channel. A "MUX" RAM 64 stores a 2-bit value to indicate which of the four available elements is connected to each channel per MUX state. Three "Chn" RAMs 66, 68 and 70 contain the coordinates for each of the four associated physical elements per channel. This two-step structure provides complete flexibility for multiplexer designs without large memories.

The delay calculator loops through 16 channels at a 40 MHz rate so that delays for all channels may be calculated at, the required 2.5 MHz rate. This is done with a 4-bit up counter 58 (see FIG. 8A), initialized with the "Start" signal. The "Start" signal is also received by a delay circuit 60. The up counter 58 outputs a 4-bit channel index (labeled "Channel" in FIG. 8) to the "Chn" RAMs 66, 68 and 70 and to another delay circuit 62. The delay circuits 60 and 62 respectively output delayed versions of the "Start" and "Channel" signals (labeled "Strt" and "Chn", respectively, in FIG. 8A). The "Strt" and "Chn" signals are output aligned with the corresponding delay and apodization data.

The 4-bit channel index is combined with an 8-bit MUX State signal to look up the element index from the "MUX" RAM 64. The resulting two-bit element index is combined with the 4-bit channel index to look up the physical element coordinates in the "Chn" RAMs 66, 68 and 70.

The "Start" signal triggers a brief initialization, followed by the pipelined delay and apodization calculation. The initialization provides for setup of the "MUX" RAM 64 and an element projection ("PROJ") RAM 92 (see FIG. 8B).

The first loop through the 16 channels, after "Start", is used to setup the element projection RAM 92 for apodization. During initialization the element positions from "Chn" RAMs 66, 68 and 70 are passed directly to the cordics via line B and multiplexer 110 (see FIG. 9) of the respective ALUs 78, 80 and 82, and the controls for the cordics 84 and 86 are set to perform a fixed-angle rotation according to AngS. The results are stored in the projection RAM 92. A second loop through the 16 channels may be used to prepare the pipes for dynamic calculations. The total initialization time is less than 0.5 μsec. Synchronizing the cordic controls with the pipeline can eliminate the need for the extra loop, reducing initialization to 0.25 μsec.

Figure 9:
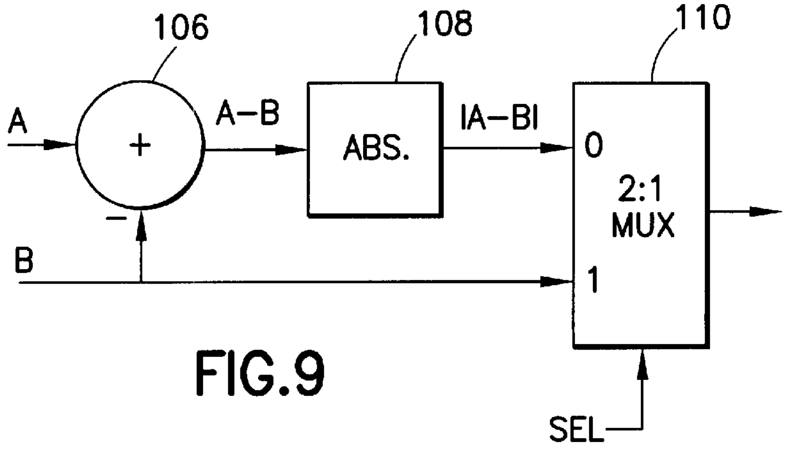
FIG. 9 is a block diagram showing a delay calculator arithmetic logic unit (ALU) in accordance with the preferred embodiment disclosed in U.S. Pat. No. 6,123,671.

After initialization the delay calculator begins updating the dynamic parameters and producing dynamic delays and apodization. For delay (see FIG. 8A), the focus coordinates from registers 72 and 74 are respectively subtracted in ALUs 78 and 80 from the element coordinates from "ChnX" RAM 66 and "ChnZ" RAM 68 and the absolute values of the coordinate differences x and z are fed to a cordic 84, and the focus coordinates from register 76 are subtracted in ALU 82 from the element coordinates from "ChnY" RAM 70 and the absolute value of the difference y is fed to cordic 88, along with the output of cordic 84. These operations performed by each ALU are depicted in FIG. 9 by adder/subtracter 106 and absolute value block 108. The adder/subtracter 106 receives the focus coordinate via line A and the element position coordinate via line B. The multiplexer 110 is switched to pass the absolute value to the respective cordic.

The first cordic 84 transforms x and z to a rotated coordinate system, x' and z'. The second cordic 86 then rotates x' and y to x" and y". The first cordic 84 calculates the hypotenuse in the x-z plane by rotating it onto x', and the second cordic 86 calculates the three-dimensional hypotenuse, now in the x'-y plane, by rotating it onto x". The calculated hypotenuse corresponds to the propagation time. The range offset time ($R_{offset}$) from register 88 is subtracted from the output of cordic 86 in adder 90 to produce the delay.

For apodization, the aperture center (Apx') from register 94 is subtracted in adder 96 from the element positions read from the projection RAM 92, in accordance with Eq. (7). The absolute value (block 98) of the resulting distance $Apx_i'$ is multiplied by the inverse aperture size (iAP) from register 100 by multiplier 102. The resulting product is used to index a window function table in "window" RAM 104, which produces an 8-bit shading (i.e., apodization) value. The "window" RAM 104 preferably stores a bank of window function tables, with one table be selected by the input "BANK".

The focus and element coordinates should all be expressed in 6.25 nsec units, pre-scaled by 1/M. Providing additional fractional bits can help maintain precision. The $R_{offset}$ is not pre-scaled by 1/M since it is after the cordics.

In the case of curved probes, the delay errors caused by the refraction of the ultrasonic waves within the lens of the probe, if not corrected for, will degrade the focusing of the ultrasound scanner. In accordance with the preferred embodiments of the present invention, the above-described agile beamformer is employed to correct the refraction delay errors on curved probes for all ranges. This is accomplished using φ, the angle from the element's rotated z axis, z', to the focus, to determine the delay correction.

Figure 10:
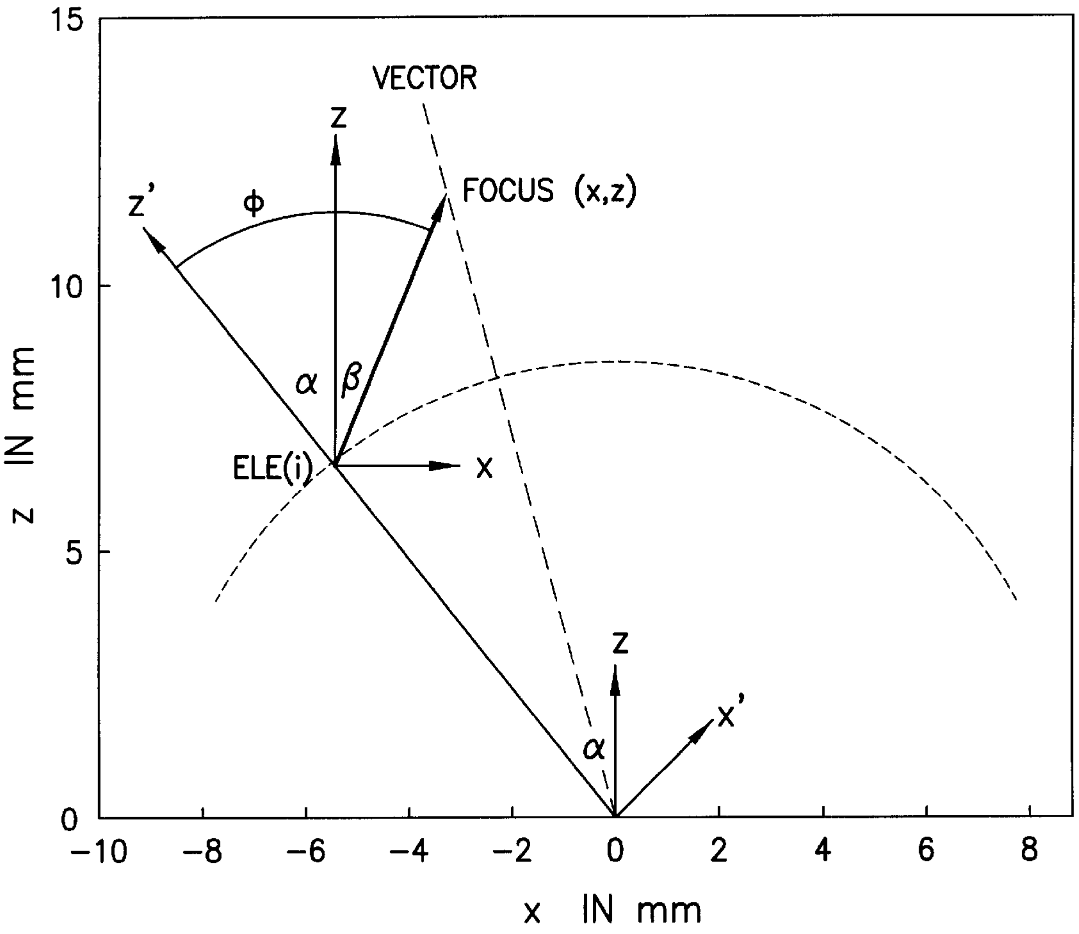
FIG. 10 is a schematic showing the geometry for agile beamformer refraction correction in accordance with preferred embodiments of the invention.

The geometry is shown in FIG. 10 for the i-th element, Ele(i), with the focus at Focus(x,z). The angle φ is mapped to a delay correction value using a look-up table (LUT), which will provide the refraction delay errors independent of range. The difficult part is calculating φ. However, the agile beamformer simplifies this calculation.

Again referring to FIG. 10, all angles are defined to be positive for counterclockwise rotations from the z axis. This means that φ is calculated as:

$$\phi=|\alpha-\beta| \tag{14}$$

α is the angle from the element's rotated z axis, z', to the element's non-rotated z axis. The angle α is element dependent only and thus can be pre-scan loaded. β is the angle from the element's z axis to a line from that element to the focus. β is element, vector, and range dependent, but β can be determined from the cordic rotators used in the receive delay calculations. A small lookup table using the bits from each rotation stage in the cordic determines β every 400 nsec. The inherent properties of the cordic rotation provide the angle from the element's z axis to the focus for each element, for every vector as a function of range. This reduces the agile beamformer calculation of to a subtraction and magnitude operation.

Figure 11:
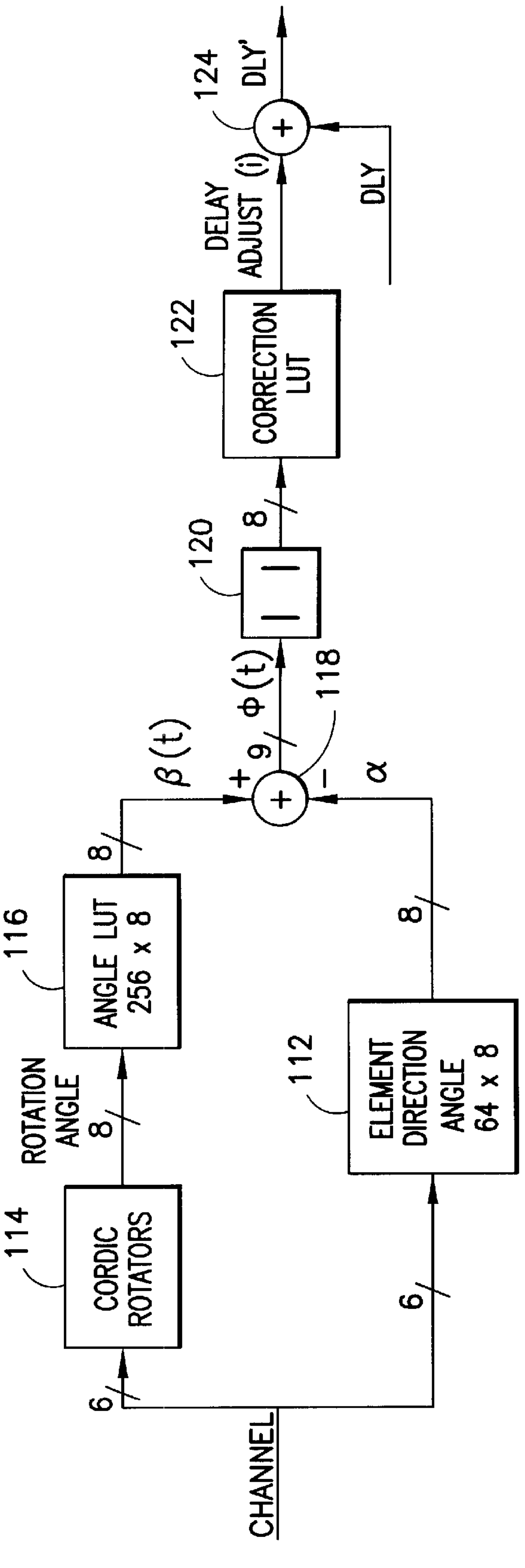
FIG. 11 is a block diagram showing the agile beamformer angular refraction correction architecture in accordance with the preferred embodiment of the invention.

FIG. 11 shows the refraction calculation section of the agile beamformer in accordance with the preferred embodiment of the invention. The six channel bits encode the 16 channels and 4 multiplexer states found in each delay calculator. The block 112 is the LUT of α as shown in FIG. 10. The cordic rotators 84, 86 from FIG. 8A are shown in dashed lines in FIG. 11 to indicate that they are the same, not additional hardware. The rotation angle is shown as eight bits out of the cordic rotators with one bit for each stage of rotation. The rotation angle is updated every 400 nsec for each of the 16 channels. The 256×8-bit angle LUT 116 then transforms the cordic angle to β as shown in FIG. 10. The values read out of the lookup tables 112 and 116 are inputted to an adder/subtracter 118, which subtracts α from β. The angle φ is then obtained by taking the absolute value (block 120) of the result of the subtraction. The value φ is then used as the index into a final correction LUT 122 that produces the delay adjustment for the i-th channel. The correction LUT 122 is pre-scan loaded with the exact refraction delay error adjustments appropriate for the specific probe which is connected to the system. This adjustment is than added to the cordic calculated delay value, Dly, to produce a refraction corrected delay value, Dly', for the i-th elements.

Simulations have been run which confirm that the disclosed agile beamformer angular refraction correction method substantially eliminates (<10 nsec error) the delay error for all ranges for curved probes.

Although the preferred embodiment has been disclosed in the context of a receive beamformer, it will be readily appreciated that the invention also has application. in transmit beamforming. To generally depict a transmit beamformer in accordance with another preferred embodiment of the invention, one need merely substitute pulsing circuits for the receive channels shown in FIG. 3.

Furthermore, FIGS. 10 and 11 show the method and apparatus of a preferred embodiment for the two-dimensional case, i.e., scanning in a plane. The disclosed technique can be extrapolated to the three-dimensional case by providing an angle LUT which is addressed with 16 bits, 8 bits representing the 8 stages of rotation of the first cordic rotator and 8 bits representing the 8 stages of rotation of the second cordic rotator. It should also be noted that the invention is not limited to use with 8-stage cordic rotators. The number of stages in the cordic rotators can be varied as desired.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. Therefore it is intended that the invention not be limited to the particular embodiment disclosed as the best mode contemplated for carrying out this invention, but that the invention will include all embodiments falling within the scope of the appended claims.

The phrase "as a function of", as used in the claims, is not to be construed to mean "as a function of only" what follows. For example, in accordance with the foregoing definition, the phrase "determine y as a function of x" would read on all cases where y was determined as a function of x alone or as a function of x and one or more other variables, e.g., z.

What is claimed is:

1. A beamforming system comprising:

a transducer array comprising a multiplicity of transducer elements;

a multiplicity of receive channels respectively operatively coupled to said multiplicity of transducer elements;

a cordic rotator connected to calculate respective hypotenuses for each transducer element to a focal position, said calculation being performed for each of a multiplicity of focal positions, each hypotenuse being a function of focal position data representing a respective focal position and transducer element position data representing the position of a respective transducer element;

an angular refraction correction circuit for outputting a delay adjustment which is a function of rotation angle data from said cordic rotator; and a time delay generator for applying respective time delays to respective receive channels, each time delay being a function of a respective hypotenuse calculation result output by said cordic rotator and a respective delay adjustment output by said angular refraction correction circuit.

2. The beamforming system as recited in claim 1, wherein said angular refraction correction circuit comprises:

first memory arranged to output an angle value α for each element which is a function of channel number and multiplexer state;

second memory arranged to output an angle value β for each element which is a function of a rotation angle output by said cordic rotator;

a subtracter for subtracting the angle value α from the angle value β and outputting a result; and third memory arranged to output a delay adjustment for each element which is a function of the absolute value of the result from said subtracter.

3. The beamforming system as recited in claim 2, wherein each of said first through third memories comprises a respective lookup table.

4. The beamforming system as recited in claim 1, wherein said cordic rotator comprises a plurality of successive stages, each stage performing a coordinate transformation that rotates the inputs to that stage, the angle of rotation becoming smaller for each successive stage.

5. A beamforming system comprising:

a transducer array comprising a multiplicity of transducer elements arranged in a plane having x and z coordinate axes; and a beamformer comprising:

a multiplicity of receive channels respectively operatively coupled to said multiplicity of transducer elements;

first memory storing x and z coordinates of a focal position;

second memory storing respective sets of coordinates of respective positions of said multiplicity of transducer elements, each coordinate set comprising an x coordinate and a z coordinate;

a first adding/subtracting circuit connected to said first and second memories for forming respective x coordinate differences between said x coordinate of said focal position and respective x coordinates of said element positions;

a second adding/subtracting circuit connected to said first and second memories for forming respective z coordinate differences between said z coordinate of said focal position and respective z coordinates of said element positions;

a cordic rotator connected to said first and second adding/subtracting circuits for performing coordinate transformations of the outputs of said first and second adding/subtracting circuits;

an angular refraction correction circuit for outputting a delay adjustment which is a function of rotation angle data from said cordic rotator; and a time delay generator for applying respective time delays to respective receive channels, each time delay being a function of a respective hypotenuse calculation result output by said cordic rotator and a respective delay adjustment out by said angular refraction correction circuit.

6. The beamforming system as recited in claim 5, wherein said angular refraction correction circuit comprises:

third memory arranged to output an angle value α for each element which is a function of channel number and multiplexer state;

fourth memory arranged to output an angle value β for each element which is a function of a rotation angle output by said cordic rotator;

a subtracter for subtracting the angle value α from the angle value β and outputting a result; and fifth memory arranged to output a delay adjustment for each element which is a function of the absolute value of the result from said subtracter.

7. The beamforming system as recited in claim 5, wherein said cordic rotator calculates a respective hypotenuse as a function of respective x and z coordinate differences and respective sign bits of respective z coordinates.

8. The beamforming system as recited in claim 5, wherein said cordic rotator comprises a plurality of successive stages, each stage performing a coordinate transformation that rotates the inputs to that stage, the angle of rotation becoming smaller for each successive stage.

9. A beamforming system comprising:

a transducer array comprising a multiplicity of transducer elements;

a multiplicity of receive channels respectively operatively coupled to said multiplicity of transducer elements;

first and second cordic rotators connected in series to calculate respective hypotenuses for each transducer element to a focal position, said calculation being performed for each of a multiplicity of focal positions, each hypotenuse being a function of focal position data representing a respective focal position and transducer element position data representing the position of a respective transducer element;

an angular refraction correction circuit for outputting a delay adjustment which is a function of rotation angle data from said first and second cordic rotators; and a time delay generator for applying respective time delays to respective receive channels, each time delay being a function of a respective hypotenuse calculation result output by said second cordic rotator and a respective delay adjustment output by said angular refraction correction circuit.

10. The beamforming system as recited in claim 9, wherein said angular refraction correction circuit comprises:

first memory arranged to output a first angle value for each element which is a function of channel number and multiplexer state;

second memory arranged to output a second angle value for each element which is a function of rotation angle data output by said first and second cordic rotators;

a subtracter for subtracting said first angle value from said second angle value and outputting a result; and fifth memory arranged to output a delay adjustment for each element which is a function of the absolute value of the result from said subtracter.

11. A beamforming system comprising:

a transducer array comprising a multiplicity of transducer elements;

a multiplicity of pulsing circuits respectively operatively coupled to said multiplicity of transducer elements;

a cordic rotator connected to calculate respective hypotenuses for each transducer element to a focal position, said calculation being performed for each of a multiplicity of focal positions, each hypotenuse being a function of focal position data representing a respective focal position and transducer element position data representing the position of a respective transducer element;

an angular refraction correction circuit for outputting a delay adjustment which is a function of rotation angle data from said cordic rotator; and a time delay generator for applying respective time delays to respective pulsing circuits, each time delay being a function of a respective hypotenuse calculation result output by said cordic rotator and a respective delay adjustment output by said angular refraction correction circuit.

12. The beamforming system as recited in claim 11, wherein said angular refraction correction circuit comprises:

first memory arranged to output an angle value α for each element which is a function of channel number and multiplexer state;

second memory arranged to output an angle value β for each element which is a function of a rotation angle output by said cordic rotator;

a subtracter for subtracting the angle value α from the angle value β and outputting a result; and third memory arranged to output a delay adjustment for each element which is a function of the absolute value of the result from said subtracter;

a time delay generator for applying respective time delays to respective pulsing circuits, each time delay being a function of a respective output of said second cordic rotator.

13. The beamforming system as recited in claim 12, wherein each of said first through third memories comprises a respective lookup table.

14. The beamforming system as recited in claim 11, wherein said cordic rotator comprises a plurality of successive stages, each stage performing a coordinate transformation that rotates the inputs to that stage, the angle of rotation becoming smaller for each successive stage.

15. A beamforming system comprising:

a transducer array comprising a multiplicity of transducer elements arranged in a plane having x and z coordinate axes; and a beamformer comprising:

a multiplicity of pulsing circuits respectively operatively coupled to said multiplicity of transducer elements;

first memory storing x and z coordinates of a focal position;

second memory storing respective sets of coordinates of respective positions of said multiplicity of transducer elements, each coordinate set comprising an x coordinate and a z coordinate;

a first adding/subtracting circuit connected to said first and second memories for forming respective x coordinate differences between said x coordinate of said focal position and respective x coordinates of said element positions;

a second adding/subtracting circuit connected to said first and second memories for forming respective z coordinate differences between said z coordinate of said focal position and respective z coordinates of said element positions;

a cordic rotator connected to said first and second adding/subtracting circuits for performing coordinate transformations of the outputs of said first and second adding/subtracting circuits;

an angular refraction correction circuit for outputting a delay adjustment which is a function of rotation angle data from said cordic rotator; and a time delay generator for applying respective time delays to respective pulsing circuits, each time delay being a function of a respective hypotenuse calculation result output by said cordic rotator and a respective delay adjustment out by said angular refraction correction circuit.

16. The beamforming system as recited in claim 15, wherein said angular refraction correction circuit comprises:

third memory arranged to output an angle value α for each element which is a function of channel number and multiplexer state;

fourth memory arranged to output an angle value β for each element which is a function of a rotation angle output by said cordic rotator;

a subtracter for subtracting the angle value α from the angle value β and outputting a result; and fifth memory arranged to output a delay adjustment for each element which is a function of the absolute value of the result from said subtracter.

17. The beamforming system as recited in claim 15, wherein said cordic rotator calculates a respective hypotenuse as a function of respective x and z coordinate differences and respective sign bits of respective z coordinates.

18. The beamforming system as recited in claim 15, wherein said cordic rotator comprises a plurality of successive stages, each stage performing a coordinate transformation that rotates the inputs to that stage, the angle of rotation becoming smaller for each successive stage.

19. A beamforming system comprising:

a transducer array comprising a multiplicity of transducer elements;

a multiplicity of pulsing circuits respectively operatively coupled to said multiplicity of transducer elements;

first and second cordic rotators connected in series to calculate respective hypotenuses for each transducer element to a focal position, said calculation being performed for each of a multiplicity of focal positions, each hypotenuse being a function of focal position data representing a respective focal position and transducer element position data representing the position of a respective transducer element;

an angular refraction correction circuit for outputting a delay adjustment which is a function of rotation angle data from said first and second cordic rotators; and a time delay generator for applying respective time delays to respective pulsing circuits, each time delay being a function of a respective hypotenuse calculation result output by said second cordic rotator and a respective delay adjustment output by said angular refraction correction circuit.

20. The beamforming system as recited in claim 19, wherein said angular refraction correction circuit comprises:

first memory arranged to output a first angle value for each element which is a function of channel number and multiplexer state;

second memory arranged to output a second angle value for each element which is a function of rotation angle data output by said first and second cordic rotators;

a subtracter for subtracting said first angle value from said second angle value and outputting a result; and third memory arranged to output a delay adjustment for each element which is a function of the absolute value of the result from said subtracter.

21. An imaging system comprising:

a transducer array comprising a multiplicity of transducer elements arranged in a plane;

a delay calculator for calculating a set of respective receive time delays as a function of a focal position and respective positions of a set of said transducer elements;

a transmit beamformer programmed to activate said transducer array to transmit a focused ultrasound beam;

a receive beamformer comprising a set of receive channels for converting respective analog signals from said set of transducer elements into respective vectors of digital samples, a channel control bus for applying said set of respective receive time delays to said respective vectors of digital samples in said set of receive channels, and a beamsummer for summing at least said time-delayed vectors of digital samples from said set of receive channels to produce a net receive signal;

a processor for deriving an image signal from said net receive signal; and a display device for displaying an image having an image portion which is a function of said image signal, wherein said delay calculator comprises:

a cordic rotator connected to calculate respective hypotenuses for each transducer element of said set to a focal position, said calculation being performed for each of a multiplicity of focal positions, each hypotenuse being a function of focal position data representing a respective focal position and transducer element position data representing the position of a respective transducer element;

an angular refraction correction circuit for outputting a delay adjustment which is a function of rotation angle data from said cordic rotator; and a time delay generator for applying respective time delays to respective receive channels of said set, each time delay being a function of a respective hypotenuse calculation result output by said cordic rotator and a respective delay adjustment output by said angular refraction correction circuit.

22. The imaging system as recited in claim 21, wherein said angular refraction correction circuit comprises:

first memory arranged to output an angle value α for each element which is a function of channel number and multiplexer state;

second memory arranged to output an angle value β for each element which is a function of a rotation angle output by said cordic rotator;

a subtracter for subtracting the angle value α from the angle value β and outputting a result; and third memory arranged to output a delay adjustment for each element which is a function of the absolute value of the result from said subtracter.

23. The imaging system as recited in claim 22, wherein each of said first through third memories comprises a respective lookup table.

24. The imaging system as recited in claim 22, further comprising a computer for generating a set of vector parameters, and a beamformer control bus for distributing said set of vector parameters to said time delay calculator, said set of receive time delays being a function of said vector parameters.

25. An imaging system comprising:

a transducer array comprising a multiplicity of transducer elements arranged in a plane;

a delay calculator for calculating a set of respective receive time delays as a function of a focal position and respective positions of a set of said transducer elements;

a transmit beamformer programmed to activate said transducer array to transmit a focused ultrasound beam;

a receive beamformer comprising a set of receive channels for converting respective analog signals from said set of transducer elements into respective vectors of digital samples, a channel control bus for applying said set of respective receive time delays to said respective vectors of digital samples in said set of receive channels, and a beamsummer for summing at least said time-delayed vectors of digital samples from said set of receive channels to produce a net receive signal;

a processor for deriving an image signal from said net receive signal; and a display device for displaying an image having an image portion which is a function of said image signal, wherein said delay calculator comprises:

first and second cordic rotators connected in series to calculate respective hypotenuses for each transducer element of said set to a focal position, said calculation being performed for each of a multiplicity of focal positions, each hypotenuse being a function of focal position data representing a respective focal position and transducer element position data representing the position of a respective transducer element;

an angular refraction correction circuit for outputting a delay adjustment which is a function of rotation angle data from said first and second cordic rotators; and a time delay generator for applying respective time delays to respective receive channels of said set, each time delay being a function of a respective hypotenuse calculation result output by said second cordic rotator and a respective delay adjustment output by said angular refraction correction circuit.

26. A method for correcting for time delay errors due to refraction during ultrasound beamforming, comprising the steps of:

storing geometry parameters of a transducer array having a multiplicity of transducer elements;

storing vector parameters for forming a focused beam having a focal position;

calculating respective hypotenuses representing the distances from said focal position to said respective transducer elements as a function of said geometry parameters and said vector parameters using multiple stages of cordic rotation to derive each hypotenuse;

determining a delay adjustment which is a function of said geometry parameters and rotation angle data used in said multiple stages of cordic rotation;

generating respective time delays as a function of said respective calculated hypotenuses and said respective delay adjustments; and forming a beam using said respective time delays.

27. The method as recited in claim 26, wherein said step of calculating a delay adjustment comprises the steps of:

determining an angle value α for each element which is a function of channel number and multiplexer state;

determining an angle value β for each element which is a function of said rotation angle data;

subtracting the angle value α from the angle value β; and determining said delay adjustment for each element which is a function of the absolute value of the result of said subtracting step.

28. The method as recited in claim 27, wherein each of said determining steps is performed by addressing a respective lookup table.

29. The method as recited in claim 26, wherein each stage of cordic rotation comprises bit shifts and additions.

30. The method as recited in claim 29, wherein each stage of cordic rotation comprises a coordinate transformation using coefficients which are powers of two.

31. A method for correcting time delays errors due to refraction during ultrasonic beamforming, comprising the steps of:

calculating a hypotenuse representing the distance from a focal position to a transducer element using cordic rotation;

calculating an angle ϕ from the normal of the transducer element to the focal position as a function of an angle of said cordic rotation;

generating a delay error correction as a function of said angle ϕ; and generating a time delay as a function of said calculated hypotenuse and said delay error correction.

* * * * *